(12) United States Patent
Trama et al.

(10) Patent No.: US 8,394,936 B2
(45) Date of Patent: Mar. 12, 2013

(54) **METHODS AND COMPOSITIONS FOR DETECTING SEROTYPES OF *CHLAMYDIA TRACHOMATIS* CAPABLE OF CAUSING LYMPHOGRANULOMA VENEREUM**

(75) Inventors: Jason Trama, Burlington, NJ (US); Eli Mordechai, Robbinsville, NJ (US); Martin E. Adelson, Hillsborough, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 165 days.

(21) Appl. No.: 11/436,506

(22) Filed: May 18, 2006

(65) Prior Publication Data
US 2007/0269810 A1 Nov. 22, 2007

(51) Int. Cl.
*C07H 21/04* (2006.01)
(52) U.S. Cl. .................................. 536/23.1; 536/24.32
(58) Field of Classification Search .................. None
See application file for complete search history.

(56) References Cited

U.S. PATENT DOCUMENTS
6,582,908 B2 * 6/2003 Fodor et al. ................... 506/9
7,041,490 B1 * 5/2006 Griffais et al. ............. 435/252.3

OTHER PUBLICATIONS

Buck, GA et al. Design Strategies and Performance of Custom DNA Sequencing Primers. 1999 Biotechniques vol. 27 No. 3 pp. 528-536.*
Carlson, John et al. Polymorphisms in the *Chlamydia trachomatis* Cytotoxin Locus Assoicated with Ocular and Genital Isolates. Dec. 2004. Infection and Immunity. vol. 72 No. 12 pp. 7063-7072.*
GenBank Accession No: AY648005 GI:55975649. *Chlamydia trachomatis* clone LGV-404 cytotoxin gene, complete sequence. Pub Dec. 2004.*
Ginzinger, David et al. Gene quantification using real time quantitative PCR: An emerging technology hits the mainstream. Experimental Hematology 2002 vol. 30 pp. 503-512.*
Sturm et al. 2005. Molecular diagnosis of lymphogranuloma venereum in patients with genital ulcer disease. Journal of Clinical Microbiology 43(6):2973-2975.

Carlson et al. 2004. Polymorphisms in the *Chlamydia trachomatis* cytotoxin locus associated with ocular and genital isolates. Infection and Immunity 72(12):7063-7072.
Gomes et al. 2004. Recombination in the genome of *Chlamydia trachomatis* involving the polymorphic membrane protein c gene relative to ompa and evidence for horizontal gene transfer. Journal of Bacteriology. 186(13):4295-4306.
Morre et al. 2005. Real-time polymerase chain reaction to diagnose lymphogranuloma venereum. Emerging Infectious Diseases 11(8):1311-1312.
Nieuwenhuis et al. 2004. Resurgence of lymphogranuloma venerum in Western Europe: an outbreak of *Chlamydia trachomatis* serovar L2 proctitis in The Netherlands among men who have sex with men. Clinical Infectious Diseases 39:996-1003. Electronically published on Sep. 8, 2004.
Yuan et al. 1989. Nucleotide and deduced amino acid sequences for the four variable domains of the major outer membrane proteins of the 15 *Chlamydia trachomatis* serovars. Infection and Immunity 57(4):1040-1049.
National Center for Biotechnology Information (NCBI) accession No. 55975647, Dec. 1, 2004.
National Center for Biotechnology Information (NCBI) accession No. 55975648 Dec. 1, 2004.
National Center for Biotechnology Information (NCBI) accession No. 55975648. Dec. 1, 2004.

* cited by examiner

*Primary Examiner* — Sarae Bausch
(74) *Attorney, Agent, or Firm* — Siu K. Lo

(57) ABSTRACT

Disclosed are methods and compositions for conducting assays of samples utilizing polymerase chain reactions ("PCRs") in the detection of serotypes of *Chlamydia trachomatis* capable of causing lymphogranuloma venereum ("LGV"). These assays take advantage of a deletion occurring in the cytotoxin gene locus specific to the L I, L II, and L serotypes. Each of these assays employs a first primer having a nucleotide sequence flanking one side of the deletion point and a second primer having a nucleotide sequence flanking the other side of the deletion point, wherein the first primer and the second primer are capable of hybridizing respectively to the plus strand and the minus strand of the genome of *Chlamydia trachomatis* during the PCR. Synthesis during the PCR of a sequence-specific amplicon containing this deletion point indicates that the sample contains nucleic acid specific to an LGV-causing serotype of *Chlamydia trachomatis*.

2 Claims, No Drawings

METHODS AND COMPOSITIONS FOR DETECTING SEROTYPES OF *CHLAMYDIA TRACHOMATIS* CAPABLE OF CAUSING LYMPHOGRANULOMA VENEREUM

BACKGROUND OF THE INVENTION

1. Field of the Invention

The invention broadly concerns methods for conducting PCR-based assays useful in the detection of LGV-causing serotypes of *Chlamydia trachomatis*. More specifically, in this invention, an assay of a sample utilizes a first primer having a nucleotide sequence flanking one side of a deletion of the cytotoxin gene locus, and a second primer having a nucleotide sequence flanking the other side of this deletion, wherein synthesis of a sequence-specific amplicon containing the point of the deletion indicates that the sample contains nucleic acid specific to an LGV-causing serotype of *Chlamydia trachomatis*.

2. Description of the Related Art

*Chlamydia trachomatis* is an obligate intracellular prokaryote. This organism includes the A, B, C, D, E, F, G, H, I, J, K, L I, L II, and L III serotypes (Carlson et al., 2004, Polymorphisms in the *Chlamydia trachomatis* cytotoxin locus associated with ocular and genital isolates. Infection and Immunity 72:7063-7072). Serotypes of the L group of *Chlamydia trachomatis* (e.g., the L I, L II, and L III serotypes) are the causative agents of LGV. This disease, which is sexually transmitted, is characterized by three stages. In the primary stage, small, painless herpetiform genital ulcers are formed which are often not recognized and resolve spontaneously. The secondary stage presents itself as lymphadenopathy usually without any genital lesions. The tertiary stage, also known as the anorectal/elephantiasis stage, is typified by permanent disfigurement resulting from destroyed inguinal lymphoid tissue (Sturm et al., 2005, Molecular diagnosis of lymphogranuloma venereum in patients with genital ulcer disease. Journal of Clinical Microbiology 43:2973-2975). Thus, a need exists to quickly identify infection of a subject by a serotype of *Chlamydia trachomatis* belonging to the L group so that a medical practitioner can intervene and administer the appropriate treatment to prevent the onset of or ameliorate the destructive tertiary stage of LGV.

SUMMARY OF THE INVENTION

The Method of the Invention

An embodiment of the invention is directed to a method for determining whether a sample from a subject contains a serotype of *Chlamydia trachomatis* capable of causing LGV comprising (a) providing a vessel containing a composition, wherein the composition contains a first primer, a second primer, and a nucleic acid from the sample, wherein the composition is capable of amplifying, by a PCR, a segment of the nucleic acid to produce an amplicon, wherein production of the amplicon is primed by the first primer and the second primer, (b) incubating the vessel under conditions allowing production of the amplicon if the sample contains the serotype of *Chlamydia trachomatis*, and (c) determining that the sample contains the serotype of *Chlamydia trachomatis* if the amplicon is detected, or determining that the sample does not contain the serotype of *Chlamydia trachomatis* if the amplicon is not detected, wherein the amplicon comprises or consists of the nucleotide sequence of SEQ ID NO:3 (wherein the deletion point of the cytotoxin gene locus is located between the a residue at position 10 and the g residue at position 11), SEQ ID NO:4 (wherein the deletion point of the cytotoxin gene locus is located between the a residue at position 11 and the g residue at position 12), SEQ ID NO:5 (wherein the deletion point of the cytotoxin gene locus is located between the a residue at position 12 and the g residue at position 13), SEQ ID NO:6 (wherein the deletion point of the cytotoxin gene locus is located between the a residue at position 13 and the g residue at position 14), SEQ ID NO:7 (wherein the deletion point of the cytotoxin gene locus is located between the a residue at position 14 and the g residue at position 15), SEQ ID NO:8 (wherein the deletion point of the cytotoxin gene locus is located between the a residue at position 15 and the g residue at position 16), SEQ ID NO:9 (wherein the deletion point of the cytotoxin gene locus is located between the a residue at position 16 and the g residue at position 17), SEQ ID NO:10 (wherein the deletion point of the cytotoxin gene locus is located between the a residue at position 17 and the g residue at position 18), SEQ ID NO:11 (wherein the deletion point of the cytotoxin gene locus is located between the a residue at position 18 and the g residue at position 19), SEQ ID NO:12 (wherein the deletion point of the cytotoxin gene locus is located between the a residue at position 19 and the g residue at position 20), SEQ ID NO:13 (wherein the deletion point of the cytotoxin gene locus is located between the a residue at position 20 and the g residue at position 21), SEQ ID NO:14 (wherein the deletion point of the cytotoxin gene locus is located between the a residue at position 21 and the g residue at position 22), SEQ ID NO:15 (wherein the deletion point of the cytotoxin gene locus is located between the a residue at position 26 and the g residue at position 27), SEQ ID NO:16 (wherein the deletion point of the cytotoxin gene locus is located between the a residue at position 31 and the g residue at position 32), SEQ ID NO:17 (wherein the deletion point of the cytotoxin gene locus is located between the a residue at position 36 and the g residue at position 37), SEQ ID NO:18 (wherein the deletion point of the cytotoxin gene locus is located between the a residue at position 41 and the g residue at position 42), SEQ ID NO:19 (wherein the deletion point of the cytotoxin gene locus is located between the a residue at position 46 and the g residue at position 47), SEQ ID NO:20 (wherein the deletion point of the cytotoxin gene locus is located between the a residue at position 56 and the g residue at position 57), SEQ ID NO:21 (wherein the deletion point of the cytotoxin gene locus is located between the a residue at position 307 and the g residue at position 308), or SEQ ID NO:22 (wherein the deletion point of the cytotoxin gene locus is located between the a residue at position 307 and the g residue at position 308), and wherein, in SEQ ID NO:22, r is a in the L I and L III serotypes, and r is g in the L II serotype; y is c in the L II serotype, and y is t in the L I and L III serotypes; and n is g in the L I and L III serotypes, and n is nothing in the L II serotype. In another embodiment, the serotype of *Chlamydia trachomatis* is the L I, L II, or L III serotype. In another embodiment, the amplicon comprises less than 1500 base pairs, less than 1400 base pairs, less than 1300 base pairs, less than 1200 base pairs, less than 1100 base pairs, less than 1000 base pairs, or less than 500 base pairs. In another embodiment, the amplicon consists of 426 base pairs. The genome of each of the L I, L II, and L III serotypes of *Chlamydia trachomatis* contains the nucleotide sequence of SEQ ID NO:1 (which is comprised by the nucleotide sequence of SEQ ID NO:23) and the nucleotide sequence of SEQ ID NO:2 (which is comprised by the nucleotide sequence of SEQ ID NO:24), wherein the nucleotide at the 3' end of SEQ ID NO:1 and the nucleotide at the 5' end of SEQ ID NO:2 are contiguous, and wherein the deletion point of the cytotoxin gene locus is located between these two nucleotides.

In another embodiment of the invention, the nucleotide sequence of SEQ ID NO:23 comprises the nucleotide sequence of the first primer. In another embodiment, the reverse complement of the nucleotide sequence of SEQ ID NO:24 comprises the nucleotide sequence of the second primer, wherein, in SEQ ID NO:24, r is a or g, y is c or t, and n is g or nothing. In another embodiment, the first primer comprises or consists of the nucleotide sequence of SEQ ID NO:25. In another embodiment, the second primer comprises or consists of the nucleotide sequence of SEQ ID NO:26. In another embodiment, the first primer is from 8 to 50 nucleotides long or is from 12 to 24 nucleotides long. In another embodiment, the second primer is from 8 to 50 nucleotides long or is from 12 to 24 nucleotides long.

In another embodiment of the invention, in (b), the first primer is capable of hybridizing to at least a portion of the reverse complement of the nucleotide sequence of SEQ ID NO:23, and in (b), the second primer is capable of hybridizing to at least a portion of the nucleotide sequence of SEQ ID NO:24, wherein, in SEQ ID NO:24, r is a or g, y is c or t, and n is g or nothing. In another embodiment, the first primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of the nucleotide sequence of SEQ ID NO:23 based on the Clustal V or W alignment method using the default parameters, and the second primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of the nucleotide sequence of SEQ ID NO:24 based on the Clustal V or W alignment method using the default parameters, wherein, in SEQ ID NO:24, r is a or g, y is c or t, and n is g or nothing. Pairwise nucleotide sequence alignments and determination of percent identities are performed using the default parameters of the Clustal V algorithm or the Clustal W algorithm, wherein both algorithms are incorporated into the Power Macintosh MegAlign 6.1 program (DNASTAR, Madison, Wis.). The default parameters for pairwise alignments using the Clustal V algorithm are as follows: Ktuple=1, gap penalty=3, window=5, and diagonals=5. The default parameters for pairwise alignments using the Clustal W algorithm are as follows: gap penalty=10.00 and gap length=0.10. The Clustal V algorithm is described in Higgins et al., 1989, Fast and sensitive multiple sequence alignments on a microcomputer. Computer Applications in the Biosciences 5:151-153. The Clustal W algorithm is described in Thompson et al., 1994, CLUSTAL W: improving the sensitivity of progressive multiple sequence alignment through sequence weighting, position specific gap penalties and weight matrix choice. Nucleic Acids Research 22:4673-80. In another embodiment, the segment of the nucleotide sequence of SEQ ID NO:23 is from 8 to 50 nucleotides long or is from 12 to 24 nucleotides long. In another embodiment, the reverse complement of the segment of the nucleotide sequence of SEQ ID NO:24 is from 8 to 50 nucleotides long or is from 12 to 24 nucleotides long, wherein, in SEQ ID NO:24, r is a or g, y is c or t, and n is g or nothing.

In another embodiment of the invention, the method further comprises detecting the amplicon using an oligonucleotide probe. In another embodiment, the oligonucleotide probe comprises or consists of the nucleotide sequence of SEQ ID NO:27. In another embodiment, a 6-carboxy-fluorescein moiety is attached to the 5' end of the oligonucleotide probe, a Black Hole Quencher 1 moiety is attached to the 3' end of the oligonucleotide probe, and the amplicon is detected by the oligonucleotide probe during real-time PCR. In another embodiment, the amplicon is detected by gel electrophoresis after the PCR is completed.

The First Composition of the Invention

An embodiment of the invention is directed to an isolated polynucleotide (e.g., the above-described amplicon) comprising or consisting of the nucleotide sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22, wherein, in SEQ ID NO:22, r is a or g, y is c or t, and n is g or nothing. In another embodiment, the polynucleotide comprises less than 1500 base pairs, less than 1400 base pairs, less than 1300 base pairs, less than 1200 base pairs, less than 1100 base pairs, less than 1000 base pairs, or less than 500 base pairs. In another embodiment, the polynucleotide consists of 426 base pairs.

The Second Composition of the Invention

An embodiment of the invention is directed to an isolated composition comprising a first oligonucleotide (e.g., the above-described first primer) and a second oligonucleotide (e.g., the above-described second primer), wherein the nucleotide sequence of SEQ ID NO:23 comprises the nucleotide sequence of the first oligonucleotide, wherein the reverse complement of the nucleotide sequence of SEQ ID NO:24 comprises the nucleotide sequence of the second oligonucleotide, and wherein, in SEQ ID NO:24, r is a or g, y is c or t, and n is g or nothing. In another embodiment, the first oligonucleotide is from 8 to 50 nucleotides long or is from 12 to 24 nucleotides long. In another embodiment, the second oligonucleotide is from 8 to 50 nucleotides long or is from 12 to 24 nucleotides long. In another embodiment, the first oligonucleotide comprises or consists of the nucleotide sequence of SEQ ID NO:25 and the second oligonucleotide comprises or consists of the nucleotide sequence of SEQ ID NO:26.

The Third Composition of the Invention

An embodiment of the invention is directed to an isolated composition comprising a first oligonucleotide (e.g., the above-described first primer) and a second oligonucleotide (e.g., the above-described second primer), wherein the first oligonucleotide is capable of hybridizing, under highly stringent hybridization conditions, to at least a portion of the reverse complement of the nucleotide sequence of SEQ ID NO:23, wherein the second oligonucleotide is capable of hybridizing, under highly stringent hybridization conditions, to at least a portion of the nucleotide sequence of SEQ ID NO:24, and wherein, in SEQ ID NO:24, r is a or g, y is c or t, and n is g or nothing. In another embodiment, the first oligonucleotide is from 8 to 50 nucleotides long or is from 12 to 24 nucleotides long. In another embodiment, the second oligonucleotide is from 8 to 50 nucleotides long or is from 12 to 24 nucleotides long.

Highly stringent hybridization conditions include the following conditions: 6×SSC and 65° C.; hybridization conditions described in Ausubel et al., 2002, Short Protocols in Molecular Biology, 5th edition, Volumes 1 and 2, John Wiley & Sons, Inc., Hoboken, N.J., the entire contents of which are hereby incorporated by reference; and hybridization conditions described in Ausubel et al., 1997, Short Protocols in Molecular Biology, 3$^{rd}$ edition, John Wiley & Sons, Inc., New York, N.Y., the entire contents of which are hereby incorporated by reference.

The Fourth Composition of the Invention

An embodiment of the invention is directed to an isolated composition comprising a first oligonucleotide (e.g., the above-described first primer) and a second oligonucleotide (e.g., the above-described second primer), wherein the first oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of the nucleotide sequence of SEQ ID NO:23 based on the Clustal V or W alignment method using the default parameters, wherein the second oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of the nucleotide sequence of SEQ ID NO:24 based on the Clustal V or W alignment method using the default parameters, and wherein, in SEQ ID NO:24, r is a or g, y is c or t, and n is g or nothing. In another embodiment, the first oligonucleotide and the second oligonucleotide are each from 8 to 50 nucleotides long or are each from 12 to 24 nucleotides long. In another embodiment, the segment of the nucleotide sequence of SEQ ID NO:23 is from 8 to 50 nucleotides long or is from 12 to 24 nucleotides long. In another embodiment, the reverse complement of the segment of the nucleotide sequence of SEQ ID NO:24 is from 8 to 50 nucleotides long or is from 12 to 24 nucleotides long, wherein, in SEQ ID NO:24, r is a or g, y is c or t, and n is g or nothing.

DETAILED DESCRIPTION

The following example illustrates the use of the methods and compositions of the invention to identify LGV-causing serotypes of Chlamydia trachomatis. This example is set forth by way of illustration only, and nothing therein shall be taken as a limitation upon the overall scope of the invention.

Example

Unless indicated otherwise, each PCR was performed in a volume of 25 μl containing extracted DNA (preferably 200 ng), 600 nM of a first primer consisting of the nucleotide sequence of SEQ ID NO:25 ("primer LGV F"), 600 nM of a second primer consisting of the nucleotide sequence of SEQ ID NO:26 ("primer LGV R"), 200 nM of an oligonucleotide probe consisting of the nucleotide sequence of SEQ ID NO:27 ("probe LGV Pr"), and IX iTaq custom supermix (Bio-Rad Laboratories, Inc., Hercules, Calif.), wherein the 2× stock solution of the iTaq custom supermix contained 120 U/ml of iTaq DNA polymerase, 80 mM Tris-HCl (pH 8.4), 200 mM KCl, 6 mM MgCl$_2$, 400 mM dATP, 400 mM dCTP, 400 mM dGTP, 800 mM dUTP, 80 U/ml of UNG, and proprietary Bio-Rad Laboratories stabilizers. Probe LGV Pr was present in the reaction mixture to monitor real-time synthesis of the amplicon resulting from each successful PCR. The primer LGV F and the primer LGV R, and the probe LGV Pr were obtained from Integrated DNA Technologies (Stokie, Ill.).

Nucleotide sequences of additional oligonucleotides potentially useful as first and second primers, and as oligonucleotide probes are determined using computer programs such as Assay Design Software 1.0.6 (Biotage, Uppsala, Sweden) and Beacon Designer 4.02 (Build 402003) (PREMIER Biosoft International, Palo Alto, Calif.).

PCRs were conducted using the Rotor-Gene 3000 platform (Corbett Research, Sydney, Australia). Parameters for each PCR were as follows: an initial incubation at 50° C. for 2 minutes to activate UNG, followed by incubation at 94° C. for 3 minutes to initially denature the DNA, inactivate the UNG, and activate the iTaq DNA polymerase. Next, 35 cycles of denaturation (94° C. for 20 seconds) and annealing and extension (60° C. for 60 seconds) were performed with fluorescence acquisition (excitation at 470 nM and emission at 510 nM) immediately following each annealing-extension step. Fluorescence curves were analyzed with dynamic-tube normalization, slope correction, and automatic threshold determination by a best-fit line of at least three standards using Rotor-Gene version 5.0 software (Corbett Research, Sydney, Australia).

The specificity of the real-time PCR was assessed by attempting to carry out the reaction with DNA extracted from each of the serotypes of Chlamydia trachomatis shown in Table 1 below. In these assays, each reaction mixture contained 200 ng of genomic DNA. Additionally, the specificity of the real-time PCR was assessed by attempting to conduct the reaction in cocktail format, wherein each reaction mixture contained DNA extracted from four or five types of pathogen as shown in Table 2 below. Cultures of organisms listed in Tables 1 and 2 were purchased from the American Type Culture Collection (ATCC®, Manassas, Va.). Only DNA from each of the L I, L II, and L III serotypes of Chlamydia trachomatis was amplified.

To determine the nucleotide sequence of each of the L I-, L II-, and L III-specific amplicons, each of these three amplicons was cloned into the pCR®2.1-TOPO® vector (Invitrogen, Carlsbad, Calif.) to create pLGVI, pLGVII, and pLGVIII, respectively. For these plasmid constructions, each PCR contained 200 ng of template DNA, 600 nM of primer LGV F, 600 nM of primer LGV R, and IX iTaq custom supermix. Parameters for each of these PCRs were as follows: incubation at 94° C. for 60 seconds, followed by 35 cycles of incubation at 94° C. for 60 seconds and 60° C. for 60 seconds, followed by a final incubation at 72° C. for 60 seconds. Sequencing of the insert of each of these three plasmids revealed that the L I-, L II-, and L III-specific amplicons were each 426 nucleotides long, and had identical nucleotide sequences, i.e., the nucleotide sequence of SEQ ID NO:21.

TABLE 1

| Serotype of Chlamydia trachomatis | ATCC ® Number |
| --- | --- |
| A | VR-571B |
| B | VR-573 |

TABLE 1-continued

| Serotype of Chlamydia trachomatis | ATCC ® Number |
|---|---|
| Ba | VR-347 |
| C | VR-1477 |
| D | VR-885 |
| E | VR-348B |
| F | VR-346 |
| G | VR-878 |
| H | VR-879 |
| I | VR-880 |
| J | VR-886 |
| K | VR-887 |
| L I | VR-901 |
| L II | VR-577 |
| L III | VR-903 |

TABLE 2

| | ATCC ® Number |
|---|---|
| Cocktail 1 | |
| Gardnerella vaginalis | 14018 |
| Neisseria gonorrhoeae | 27628 |
| Trichomonas vaginalis | 30246 |
| Ureaplasma urealyticum | 27618 |
| Cocktail 2 | |
| Bacteroides fragilis | 23745 |
| Mobiluncus curtisii | 35241 |
| Mobiluncus mulieris | 35243 |
| HTLV-1 | CRL-8294 |
| Human herpesvirus (HHV-6) | VR-1467 |
| Cocktail 3 | |
| Herpes simplex virus (HSV) Type 1 | VR-734 |
| HSV-2 | VR-734 |
| Human Papillomavirus (HPV) | CRL-1550 |

TABLE 2-continued

| | ATCC ® Number |
|---|---|
| Epstein-Barr virus (EBV) | CCL-86 |
| Cytomegalovirus (CMV) | VR-807 |
| Cocktail 4 | |
| Candida albicans | 11651 |
| Candida glabrata | 2001 |
| Candida parapsilosis | 22019 |
| Candida tropicalis | 13803 |
| Aspergillus fumigatus | 14110 |
| Cocktail 5 | |
| Mycoplasma fermentans | 15474 |
| Mycoplasma pneumoniae | 15377 |
| Mycoplasma genitalium | 33530 |
| Mycoplasma salivarium | 14277 |
| Mycoplasma hominis | 14027 |
| Cocktail 6 | |
| Human herpesvirus-8 (HHV-8) | CRL-2230 |
| Adenovirus | VR-1 |
| Coxsackie Virus | VR-184 |
| Crytococcus neoformans | 2344 |
| Babesia microti | 30222 |
| Cocktail 7 | |
| Chlamydia pneumoniae | VR-1356 |
| Helicobacter pylori | 43579 |
| Brucella abortis | 25840 |
| Borrelia burgdorferi | 35210 |
| Cocktail 8 | |
| Bartonella henselae | 49882 |
| Bartonella bacilliformis | 35656 |
| Bartonella quintana | 51694 |
| Anaplasma phagocytophila | VR-367 |
| Trichosporan | 4151 |

The invention claimed is:

1. An amplicon consisting of the nucleotide sequence of SEQ ID NO: 22, wherein r is a or g, y is c or t, and n is g.

2. An amplicon consisting of the nucleotide sequence of SEQ ID NO: 24, wherein r is a or g, y is c or t, and n is g.

* * * * *

SEQUENCE LISTING

<160> NUMBER OF SEQ ID NOS: 27

<210> SEQ ID NO 1
<211> LENGTH: 281
<212> TYPE: DNA
<213> ORGANISM: Chlamydia trachomatis

<400> SEQUENCE: 1

```
tcgaactttc tcattccaaa gattctgggc ctgctaatcc tatattatca ggtcgaaatg    60
gttttttctt ctgaaaactc ttgctttatg gtagattctc cgaacgtttt ctatgcagca   120 tgtgtaaatac ttcttaatta gaggtaagag taatgtggac ggacatactt tcagtctgcg   180
agattactat atctacaacc acaatgacat ttgcggtcga aagtatgatt cctatccact   240
aaggttttat tgaaatccag ttgataaaga agttttccta a                        281
```

<210> SEQ ID NO 2
<211> LENGTH: 119
<212> TYPE: DNA
<213> ORGANISM: Chlamydia trachomatis

<400> SEQUENCE: 2

```
gcaatgaaat tctatactta cactgcattc atgctttgga atcttcggga tagagcaaga    60
ggagagtcga agagagcgaa ggcttatgat aattaccttc tgaagcttgt atgtccttg    119
```

```
<210> SEQ ID NO 3
<211> LENGTH: 20
<212> TYPE: DNA
<213> ORGANISM: Chlamydia trachomatis

<400> SEQUENCE: 3
gttttcctaa gcaatgaaat                                                     20

<210> SEQ ID NO 4
<211> LENGTH: 22
<212> TYPE: DNA
<213> ORGANISM: Chlamydia trachomatis

<400> SEQUENCE: 4
agttttccta agcaatgaaa tt                                                  22

<210> SEQ ID NO 5
<211> LENGTH: 24
<212> TYPE: DNA
<213> ORGANISM: Chlamydia trachomatis

<400> SEQUENCE: 5
aagttttcct aagcaatgaa attc                                                24

<210> SEQ ID NO 6
<211> LENGTH: 26
<212> TYPE: DNA
<213> ORGANISM: Chlamydia trachomatis

<400> SEQUENCE: 6
gaagttttcc taagcaatga aattct                                              26

<210> SEQ ID NO 7
<211> LENGTH: 28
<212> TYPE: DNA
<213> ORGANISM: Chlamydia trachomatis

<400> SEQUENCE: 7
agaagttttc ctaagcaatg aaattcta                                            28

<210> SEQ ID NO 8
<211> LENGTH: 30
<212> TYPE: DNA
<213> ORGANISM: Chlamydia trachomatis

<400> SEQUENCE: 8
aagaagtttt cctaagcaat gaaattctat                                          30

<210> SEQ ID NO 9
<211> LENGTH: 32
<212> TYPE: DNA
<213> ORGANISM: Chlamydia trachomatis

<400> SEQUENCE: 9
aaagaagttt tcctaagcaa tgaaattcta ta                                       32

<210> SEQ ID NO 10
<211> LENGTH: 35
<212> TYPE: DNA
<213> ORGANISM: Chlamydia trachomatis

<400> SEQUENCE: 10
taaagaagtt ttcctaagca atgaaattct atact                                    35
```

```
<210> SEQ ID NO 11
<211> LENGTH: 37
<212> TYPE: DNA
<213> ORGANISM: Chlamydia trachomatis

<400> SEQUENCE: 11
ataaagaagt tttcctaagc aatgaaattc tatactt                        37

<210> SEQ ID NO 12
<211> LENGTH: 39
<212> TYPE: DNA
<213> ORGANISM: Chlamydia trachomatis

<400> SEQUENCE: 12
gataaagaag ttttcctaag caatgaaatt ctatactta                      39

<210> SEQ ID NO 13
<211> LENGTH: 41
<212> TYPE: DNA
<213> ORGANISM: Chlamydia trachomatis

<400> SEQUENCE: 13
tgataaagaa gttttcctaa gcaatgaaat tctatactta c                   41

<210> SEQ ID NO 14
<211> LENGTH: 43
<212> TYPE: DNA
<213> ORGANISM: Chlamydia trachomatis

<400> SEQUENCE: 14
ttgataaaga gttttcctaa agcaatgaaa ttctatactt aca                 43

<210> SEQ ID NO 15
<211> LENGTH: 53
<212> TYPE: DNA
<213> ORGANISM: Chlamydia trachomatis

<400> SEQUENCE: 15
tccagttgat aaagaagttt tcctaagcaa tgaaattcta tacttacact gca      53

<210> SEQ ID NO 16
<211> LENGTH: 63
<212> TYPE: DNA
<213> ORGANISM: Chlamydia trachomatis

<400> SEQUENCE: 16
tgaaatccag ttgataaaga agttttccta agcaatgaaa ttctatactt acactgcatt   60
cat                                                             63

<210> SEQ ID NO 17
<211> LENGTH: 73
<212> TYPE: DNA
<213> ORGANISM: Chlamydia trachomatis

<400> SEQUENCE: 17
tttattgaaa tccagttgat aaagaagttt tcctaagcaa tgaaattcta tacttacact   60
gcattcatgc ttt                                                  73

<210> SEQ ID NO 18
<211> LENGTH: 83
<212> TYPE: DNA
<213> ORGANISM: Chlamydia trachomatis
```

```
<400> SEQUENCE: 18
aaggttttat tgaaatccag ttgataaaga agttttccta agcaatgaaa ttctatactt    60
acactgcatt catgctttgg aat                                            83

<210> SEQ ID NO 19
<211> LENGTH: 93
<212> TYPE: DNA
<213> ORGANISM: Chlamydia trachomatis

<400> SEQUENCE: 19
ccactaaggt tttattgaaa tccagttgat aaagaagttt tcctaagcaa tgaaattcta    60
tacttacact gcattcatgc tttggaatct tcg                                 93

<210> SEQ ID NO 20
<211> LENGTH: 113
<212> TYPE: DNA
<213> ORGANISM: Chlamydia trachomatis

<400> SEQUENCE: 20
tgattcctat ccactaaggt tttattgaaa tccagttgat aaagaagttt tcctaagcaa    60
tgaaattcta tacttacact gcattcatgc tttggaatct tcgggataga gca          113

<210> SEQ ID NO 21
<211> LENGTH: 426
<212> TYPE: DNA
<213> ORGANISM: Chlamydia trachomatis

<400> SEQUENCE: 21
aaatagaggg aatctgtttt ggctaatcga actttctcat tccaaagatt ctgggcctgc    60
taatcctata ttatcaggtc gaaatggttt ttcttctga aaactcttgc tttatggtag   120
attctccgaa cgttttctat gcagcatgtg taatacttct taattagagg taagagtaat   180
gtggacggac atactttcag tctgcgagat tactatatct acaaccacaa tgacatttgc   240
ggtcgaaagt atgattccta ccactaagg ttttattgaa atccagttga taagaagtt    300 ttcctaagca atgaaattct atacttacac tgcattcatg ctttggaatc ttcgggatag   360
agcaagagga gagtcgaaga gagcgaaggc ttatgataat taccttctga agcttgtatg   420
tccttg                                                              426

<210> SEQ ID NO 22
<211> LENGTH: 869
<212> TYPE: DNA
<213> ORGANISM: Chlamydia trachomatis
<220> FEATURE:
<221> NAME/KEY: misc_feature
<222> LOCATION: (714)..(714)
<223> OTHER INFORMATION: n is a, c, g, or t

<400> SEQUENCE: 22
aaatagaggg aatctgtttt ggctaatcga actttctcat tccaaagatt ctgggcctgc    60
taatcctata ttatcaggtc gaaatggttt ttcttctga aaactcttgc tttatggtag   120
attctccgaa cgttttctat gcagcatgtg taatacttct taattagagg taagagtaat   180
gtggacggac atactttcag tctgcgagat tactatatct acaaccacaa tgacatttgc   240
ggtcgaaagt atgattccta ccactaagg ttttattgaa atccagttga taagaagtt    300 ttcctaagca atgaaattct atacttacac tgcattcatg ctttggaatc ttcgggatag   360
agcaagagga gagtcgaaga gagcgaaggc ttatgataat taccttctga agcttgtatg   420
```

```
tccttggata cagctgggaa gcctcactgg aaaatccctg aaggattctt gcaatttgca      480
tttgcttccg ttcttgggta gagcattggg cgaaaaagtc tctaagaaga ggatctctca      540
ttcagctccc tgcacgargc attcaggtgt cgttgattac aacgcaaaca ggatactttg      600
ctcggcagaa yagacgagga gggttccaag tcttctatag tatttacgga ttagaaggga      660
aagtgcaacc acaccaagct cctggagata tgctatgcga cattactgaa gacntagtgt      720
taacggtcaa agatgtggat gaaagcgact accaacagaa acgaatttat gtggttttag      780
atttagcgac ggaagaagag cgtaggttgc gagcagataa gaacgtgatc cttattccta      840
gaggggagaa ttctaagaaa agaaaataa                                        869

<210> SEQ ID NO 23
<211> LENGTH: 307
<212> TYPE: DNA
<213> ORGANISM: Chlamydia trachomatis

<400> SEQUENCE: 23
aaatagaggg aatctgtttt ggctaatcga actttctcat tccaaagatt ctgggcctgc       60
taatcctata ttatcaggtc gaaatggttt tttcttctga aaactcttgc tttatggtag      120
attctccgaa cgttttctat gcagcatgtg taatacttct taattagagg taagagtaat      180
gtggacggac atactttcag tctgcgagat tactatatct acaaccacaa tgacatttgc      240
ggtcgaaagt atgattccta tccactaagg ttttattgaa atccagttga taaagaagtt      300
ttcctaa                                                                307

<210> SEQ ID NO 24
<211> LENGTH: 562
<212> TYPE: DNA
<213> ORGANISM: Chlamydia trachomatis
<220> FEATURE:
<221> NAME/KEY: misc_feature
<222> LOCATION: (407)..(407)
<223> OTHER INFORMATION: n is a, c, g, or t

<400> SEQUENCE: 24
gcaatgaaat tctatactta cactgcattc atgctttgga atcttcggga tagagcaaga       60
ggagagtcga agagagcgaa ggcttatgat aattaccttc tgaagcttgt atgtccttgg      120
atacagctgg gaagcctcac tggaaaatcc ctgaaggatt cttgcaattt gcatttgctt      180
ccgttcttgg gtagagcatt gggcgaaaaa gtctctaaga gaggatctc tcattcagct      240 ccctgcacga rgcattcagg tgtcgttgat tacaacgcaa acaggatact tgctcggca      300 gaayagacga ggagggttcc aagtcttcta tagtatttac ggattagaag ggaaagtgca      360
accacaccaa gctcctggag atatgctatg cgacattact gaagacntag tgttaacggt      420
caaagatgtg gatgaaagcg actaccaaca gaaacgaatt tatgtggttt tagatttagc      480
gacggaagaa gagcgtaggt tgcgagcaga taagaacgtg atccttattc ctagagggga      540
gaattctaag aaaagaaaat aa                                               562

<210> SEQ ID NO 25
<211> LENGTH: 26
<212> TYPE: DNA
<213> ORGANISM: Chlamydia trachomatis

<400> SEQUENCE: 25
aaatagaggg aatctgtttt ggctaa                                            26
```

-continued

```
<210> SEQ ID NO 26
<211> LENGTH: 24
<212> TYPE: DNA
<213> ORGANISM: Chlamydia trachomatis

<400> SEQUENCE: 26
caaggacata caagcttcag aagg                                      24

<210> SEQ ID NO 27
<211> LENGTH: 30
<212> TYPE: DNA
<213> ORGANISM: Chlamydia trachomatis

<400> SEQUENCE: 27
tctcttcgac tctcctcttg ctctatcccg                                30
```